(12) United States Patent
Ramasamy et al.

(10) Patent No.: US 6,455,508 B1
(45) Date of Patent: Sep. 24, 2002

(54) METHODS FOR TREATING DISEASES WITH TIRAZOLE AND PYRROLO-PYRIMIDINE RIBOFURANOSYL NUCLEOSIDES

(76) Inventors: Kanda S. Ramasamy, ICN Pharmaceuticals, Inc., 3300 Hyland Ave., Costa Mesa, CA (US) 92626; Robert Tam, ICN Pharmaceuticals, Inc., 3300 Hyland Ave., Costa Mesa, CA (US) 92626

(*) Notice: Subject to any disclaimer, the term of this patent is extended or adjusted under 35 U.S.C. 154(b) by 0 days.

(21) Appl. No.: 09/595,365

(22) Filed: Oct. 5, 2000

Related U.S. Application Data

(60) Provisional application No. 60/182,676, filed on Feb. 15, 2000.

(51) Int. Cl.[7] ............................................. A61K 31/70
(52) U.S. Cl. ............................. 514/43; 514/44; 514/45; 536/26.9; 536/27.2
(58) Field of Search ............................. 514/43, 44, 45; 536/26.9, 27.2

(56) References Cited

U.S. PATENT DOCUMENTS

| | | | | |
|---|---|---|---|---|
| 3,798,209 A | | 3/1974 | Witkowski et al. | |
| 3,962,211 A | * | 6/1976 | Townsend et al. | |
| 3,984,396 A | | 10/1976 | Witkowski et al. | |
| 3,991,078 A | | 11/1976 | Witkowski et al. | |
| 4,093,624 A | | 6/1978 | Revankar et al. | |
| RE29,835 E | | 11/1978 | Witkowski et al. | |
| 4,892,865 A | * | 1/1990 | Townsend et al. | |

FOREIGN PATENT DOCUMENTS

JP     64-026593 A     1/1989

OTHER PUBLICATIONS

DeClercq et al., Antimicrobial Agents and Chemotherapy, vol. 29, No. 3, pp. 482–487 (Mar. 1986).*
Gabrielsen et al., J. Med. Chem., vol. 35, No. 17, pp. 3231–3238 (Aug. 1992).*

* cited by examiner

*Primary Examiner*—James O. Wilson
(74) *Attorney, Agent, or Firm*—Fish & Associates, LLP; Robert D. Fish

(57) ABSTRACT

Novel heterocyclic aromatic compounds are disclosed. The novel compounds or pharmaceutically acceptable esters or salts thereof may be used in pharmaceutical compositions, and such compositions may be used to treat an infection, an infestation, a neoplasm, or an autoimmune disease. The novel compounds may also be used to modulate aspects of the immune system, including modulation of Type 1 and Type 2 activity.

12 Claims, 4 Drawing Sheets

Scheme 1

METHODS FOR TREATING DISEASES WITH TIRAZOLE AND PYRROLO-PYRIMIDINE RIBOFURANOSYL NUCLEOSIDES

This application claims the benefit of U.S. provisional application No. 60/182676, incorporated herein by reference in its entirety.

FIELD OF THE INVENTION

The present invention relates to the field of heterocyclic aromatic compounds and nucleosides.

BACKGROUND OF THE INVENTION

Mammalian immune systems contain two major classes of lymphocytes: B lymphocytes (B cells), which originate in the bone marrow; and T lymphocytes (T cells) that originate in the thymus. B cells are largely responsible for humoral immunity (i.e., antibody production), while T cells are largely responsible for cell-mediated immunity.

T cells are generally considered to fall into two subclasses, helper T cells and cytotoxic T cells. Helper T cells activate other lymphocytes, including B cells and cytotoxic T cells, and macrophages, by releasing soluble protein mediators called cytokines that are involved in cell-mediated immunity. As used herein, lymphokines are a subset of cytokines.

Helper T cells are also generally considered to fall into two subclasses, Type 1 and Type 2. Type 1 cells produce interleukin 2 (IL-2), tumor necrosis factor (TNFα) and interferon gamma (IFNγ), and are responsible primarily for cell-mediated immunity such as delayed type hypersensitivity and antiviral immunity. In contrast, Type 2 cells produce interleukins, IL4, IL-5, IL-6, IL-9, IL-10 and IL-13, and are primarily involved in assisting humoral immune responses such as those seen in response to allergens, e.g. IgE and IgG4 antibody isotype switching (Mosmann, 1989, *Annu Rev Imniunol*, 7:145–173).

As used herein, the terms Type 1 and Type 2 "responses" are meant to include the entire range of effects resulting from induction of Type 1 and Type 2 lymphocytes, respectively. Among other things, such responses include variation in production of the corresponding cytokines through transcription, translation, secretion and possibly other mechanisms, increased proliferation of the corresponding lymphocytes, and other effects associated with increased production of cytokines, including motility effects.

Previous application Nos. (09/291903, 09/471513, 60/164365, 60/164366, 60/172097, 60/175111), each of which is incorporated herein by reference, relate to aspects of our recent discoveries involving the effect of various nucleosides (which are defined herein to include derivatives and analogs of native nucleosides) on selectively modulating lymphocyte responses relative to each other. Among other things, we have shown that either of Type 1 and Type 2 responses can be selectively suppressed while the other is either induced or left relatively unaffected, and either of Type 1 or Type 2 responses can be selectively induced while the other is either suppressed or left relatively unaffected. We have also discovered the surprising fact that some nucleosides effective in selectively modulating Type 1 and Type 2 responses relative to one another tend to have a bimodal effect. Among other things, some nucleosides that tend to generally suppress or induce both Type 1 and Type 2 activity at a relatively higher dose tend to selectively modulate Type 1 and Type 2 relative to each other at relatively lower doses.

The effect of other heterocyclic aromatic compounds on selectively modulating lymphocyte responses relative to each other has not been previously studied or documented. We have discovered that the bimodal effect, or selective modulation of Type 1 and Type 2 responses relative to one another, also occurs after administration of other heterocyclic aromatic compounds.

Despite the existence of as-yet undefined mechanisms, we have discovered that enormous potential benefits can be derived from selective modulation of Type 1 and Type 2 responses relative to each other. We have concluded, for example, that specific modulation of Type 1 relative to Type 2 can be useful in treating a wide variety of conditions and diseases, ranging from infections, infestations, tumors and hypersensitivities to autoimmune diseases.

These discoveries are especially significant because modem treatment strategies for many of the above-listed diseases have limited effectiveness, significant side effects, or both. Treatment of autoimmune disease, for example, is frequently limited to palliative measures, removal of toxic antibodies (as in myasthenia gravis), and administration of hazardous drugs including corticosteroids, chloroquine derivatives, and antimetabolic or antitumor drugs, and drugs such as cyclosporines that target immune system cells.

SUMMARY

The present invention is directed to novel heterocyclic aromatic compounds, their therapeutic uses and synthesis.

In one aspect of the invention, there are provided heterocyclic aromatic compounds of Formula 1:

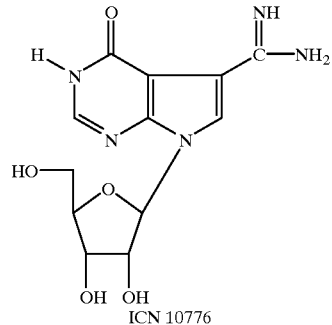

Formula 1

ICN 10776

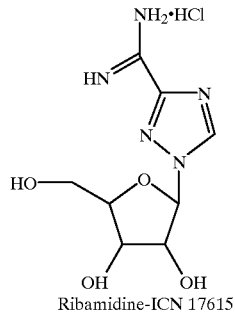

Formula 2

Ribamidine-ICN 17615

In yet another aspect of the invention, a pharmaceutical composition comprises a therapeutically effective amount of a Formula 1 carboxamidine, or a pharmaceutically acceptable ester or salt thereof admixed with at least one pharmaceutically acceptable carrier.

In still yet another aspect of the invention, a pharmaceutical composition comprises a therapeutically effective amount of a Formula 2 carboxamidine, or a pharmaceutically acceptable ester or salt thereof admixed with at least one pharmaceutically acceptable carrier.

In a further aspect of the invention, a compound according to Formulas 1 or Formula 2 are used in the treatment of any condition which responds positively to administration of the compound, and according to any formulation and protocol which achieves the positive response. Among other things, it is contemplated that compounds of Formula 1 or Formula 2 may be used to treat an infection, an infestation, a cancer, tumor or other neoplasm, giant cell arteritis, or an autoimmune disease.

DETAILED DESCRIPTION

Figure 1:
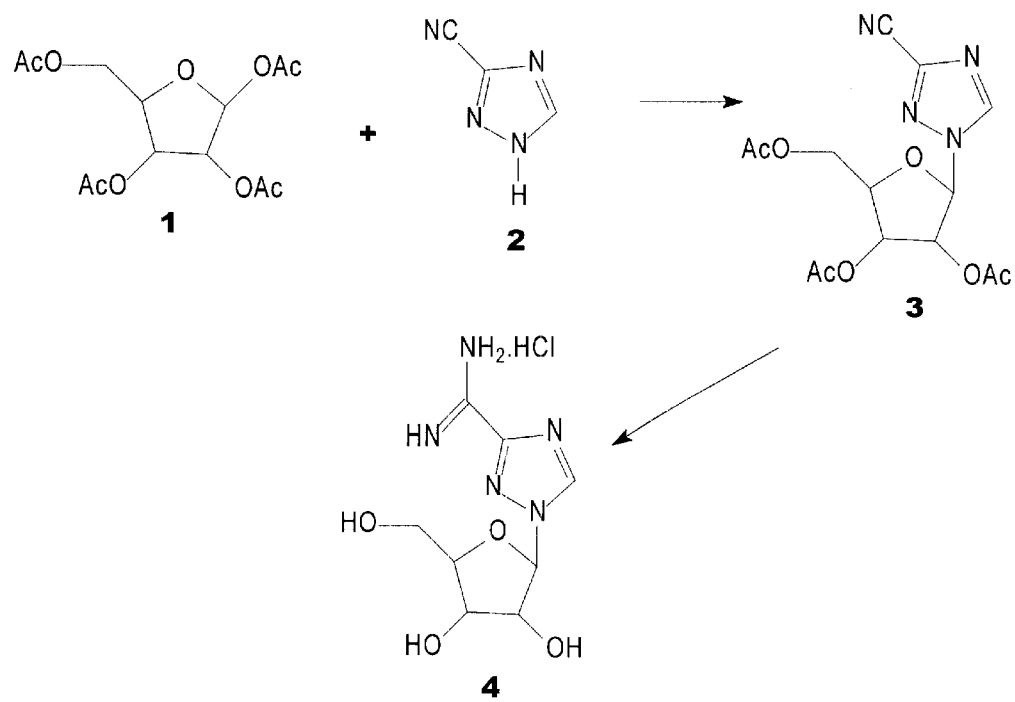
FIG. 1 depicts synthetic chemical steps that may be used to synthesize some of the compounds according to the present invention. Schemes pertaining to the synthesis of a particular composition are referenced in the examples set forth herein.

Where the following terms are used in this specification, they are used as defined below.

The terms "nucleoside" and "heterocyclic aromatic compound" are interchangeable and refer to a compound composed of any pentose or modified pentose moiety attached to a specific position of a heterocycle, aromatic heterocycle or to the natural position of a purine (9-position) or pyrimidine (1-position) or to the equivalent position in an analog.

The term "nucleotide" refers to a phosphate ester substituted on the 5'-position of a nucleoside.

The term "heterocycle" refers to a monovalent saturated or unsaturated carbocyclic radical having at least one hetero atom, such as N, O or S, within the ring each available position of which can be optionally substituted, independently, with, e.g., hydroxy, oxo, amino, imino, lower alkyl, bromo, chloro and/or cyano. Included within this class of substituents are purines, pyrimidines.

The term "purine" refers to nitrogenous bicyclic heterocycles.

The term "pyrimidine" refers to nitrogenous monocyclic heterocycles.

The term "D-nucleosides" refers to the nucleoside compounds that have a D-ribose sugar moiety (e.g., Adenosine).

The term "L-nucleosides" refers to the nucleoside compounds that have an L-ribose sugar moiety.

The terms "L-configuration" and "D-configuration" are used throughout the present invention to describe the chemical configuration of the riboftiranosyl moiety of the compounds that is linked to the pyrrolo-pyrimidone portion of the molecule.

The term "C-nucleosides" is used throughout the specification to describe the linkage type that formed between the ribose sugar moiety and the heterocyclic base. In C-nucleosides, the linkage originates from the C-1 position of the ribose sugar moiety and joins the carbon of the heterocyclic base. The linkage that forms in C-nucleosides is carbon-to-carbon type.

The term "N-nucleosides" is used throughout the specification to describe the linkage type that formed between the ribose sugar moiety and the heterocyclic base. In N-nucleosides, the linkage originates from the C-1 position of the ribose sugar moiety and joins the nitrogen of the heterocyclic base. The linkage that forms in N-nucleosides is carbon to nitrogen type.

The term "protecting group" refers to a chemical group that is added to, oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term "lower alkyl" refers to methyl, ethyl, n-propyl, isopropyl, n-butyl, t-butyl, i-butyl or n-hexyl. This term is further exemplified to a cyclic, branched or straight chain from one to six carbon atoms.

The term "aryl" refers to a monovalent unsaturated aromatic carbocyclic radical having a single ring (e.g., phenyl) or two condensed rings (e.g., naphthyl), which can optionally be substituted with hydroxyl, lower alky, chloro, and/or cyano.

The term "heterocycle" refers to a monovalent saturated or unsaturated carbocyclic radical having at least one hetero atom, such as N, O, S, Se or P, within the ring, each available position of which can be optionally substituted or unsubstituted, independently, with hydroxy, oxo, amino, imino, lower alkyl, bromo, chloro, and/or cyano.

The term "monocyclic" refers to a monovalent saturated carbocyclic radical having at least one hetero atom, such as O, N, S, Se or P, within the ring, each available position of which can be optionally substituted, independently, with a sugar moiety or any other groups like bromo, chloro and/or cyano, so that the monocyclic ring system eventually aromatized [e.g., Thymidine].

The term "immunomodulators" refers to natural or synthetic products capable of modifying the normal or aberrant immune system through stimulation or suppression.

The term "effective amount" refers to the amount of a compound of formula (I) that will restore immune function to normal levels, or increase immune function above normal levels in order to eliminate infection.

The compounds of Formula 1 may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formula 1.

The compounds of Formula 2 may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formula 2.

The term "α" and "β" indicate the specific stereochemical configuration of a substituent at an asymmetric carbon atom in a chemical structure as drawn.

The term "enantiomers" refers to a pair of stereoisomers that are non-superimposable mirror images of each other. A mixture of a pair of enantiomers, in a 1:1 ratio, is a "racemic" mixture.

The term "isomers" refers to different compounds that have the same formula. "Stereoisomers" are isomers that differ only in the way the atoms are arranged in space.

"Pharmaceutically acceptable salts" may be any salts derived from inorganic and organic acids or bases.

COMPOUNDS

The heterocyclic aromatic compounds of the present invention are generally described by Formula 1:

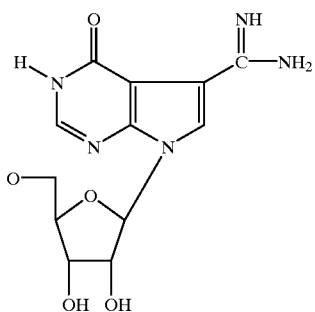

Formula 1 wherein the chemical configuration may be as the L-configuration or the D-configuration; and by Formula 2:

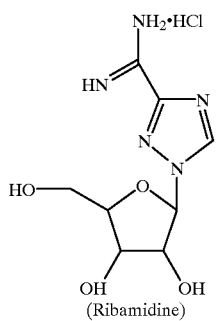

Formula 2

(Ribamidine)

wherein the chemical configuration may be as the L-configuration or the D-configuration.

USES

It is contemplated that compounds according to Formula 1 and Formula 2, the compounds of the present invention, will be used to treat a wide variety of conditions, and in fact any condition which responds positively to administration of one or more of the compounds. Among other things it is specifically contemplated that compounds of the invention may be used to treat an infection, an infestation, a cancer or tumor or an autoimmune disease.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles, and fungus.

Infestations contemplated to be treated with the compounds of the present invention include protozoan infestations, as well as helminth and other parasitic infestations.

Cancers or tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis, rheumatoid arthritis, rejection of transplantation, giant cell arteritis, allergy and asthma.

Still other contemplated uses of the compounds according to the present invention include use as intermediates in the chemical synthesis of other nucleoside or nucleotide analogs that are, in turn, useful as therapeutic agents or for other purposes.

Figure 2:
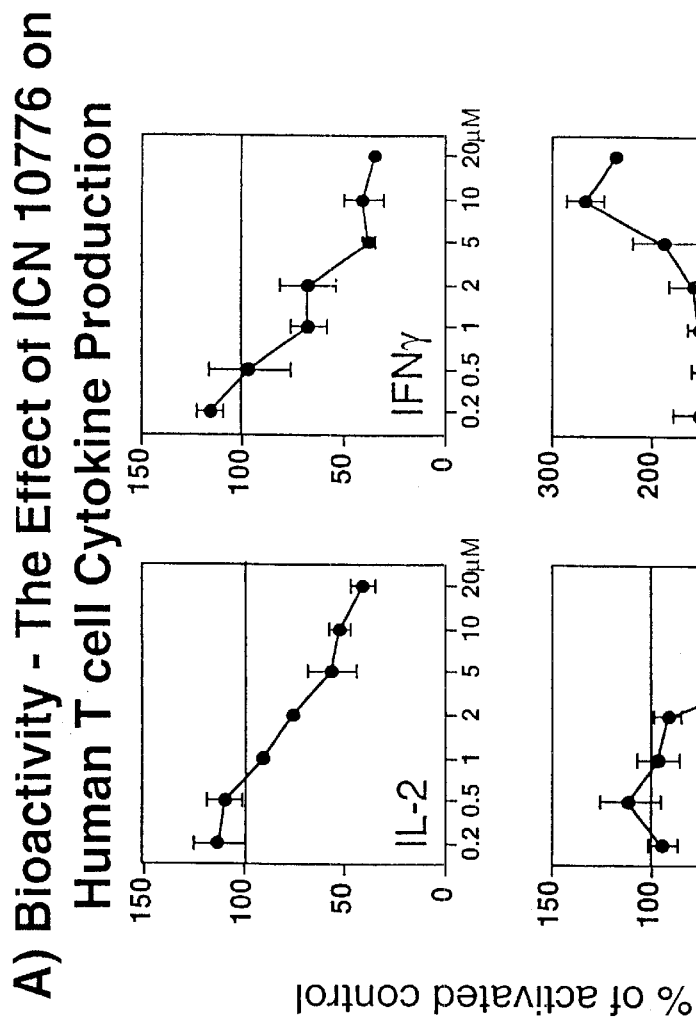
FIG. 2 is a graphical depiction of some of the compounds according to the present invention on human T cell cytokine production.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Type 1 and Type 2. (FIG. 2 ) Where modulation of Type 1 and Type 2 lymphokines occurs, it is contemplated that the modulation may include suppression of both Type 1 and Type 2, or suppression of Type 1 and stimulation of Type 2.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may attain because L-nucleosides may not be recognized by enzymes, and therefore may have longer half-lives.

It is contemplated that compounds according to the present invention will be administered in any appropriate pharmaceutical formulation, and under any appropriate protocol. Thus, administration may take place orally, parenterally (including subcutaneous injections, intravenous, intramuscularly, by intrastemal injection or infusion techniques), by inhalation spray, or rectally, topically and so forth, and in dosage unit formulations containing conventional non-toxic pharmaceutically acceptable carriers, adjuvants and vehicles.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to a targeted site within the host organism or patient to maximize the intended effect of the compound.

In addition, compounds according to the present invention may be administered alone or in combination with other agents for the treatment of the above infections or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect. Preferably, the combination therapy involves the administration of one compound of the present invention or a physiologically functional derivative thereof and one of the agents mentioned herein below.

Examples of other drugs or active ingredients contemplated to be effective in combination with a modulator selected from Formula 1 or Formula 2 are anti-viral agents such as interferon, including but not limited to interferon $\alpha$ and $\gamma$, Ribavirin, acyclovir, and AZT™; anti-fungal agents such as tolnaftate, Fungizone™, Lotrimin™, Mycelex™, Nystatin and Amphoteracin; anti-parasitics such as Mintezol™, Niclocide™, Vermox™, and Flagyl™, bowel agents such as Immodium™, Lomotil™ and Phazyme™; anti-tumor agents such as interferon $\alpha$ and $\gamma$, Adriamycin™, Cytoxan™, Imuran™, Methotrexate, Mithracin™, Tiazofurin™, Taxol™; dermatologic agents such as Aclovate™, Cyclocort™, Denorex™, Florone™, Oxsoralen™, coal tar and salicylic acid; migraine preparations such as ergotamine compounds; steroids and immunosuppresants not listed above, including cyclosporins, Diprosone™, hydrocortisone; Floron™, Lidex™, Topicort and Valisone; and metabolic agents such as insulin, and other drugs which may not nicely fit into the above categories, including cytokines such as IL2, IL4, IL6, IL8, IL10 and IL12. Especially preferred primary drugs are AZT, 3TC, 8-substituted guanosine analogs, 2,3-dideoxynucleosides, interleukin II, interferons such as I$\alpha$B-interferons, tucaresol, levamisole, isoprinosine and cyclolignans.

Examples of such further therapeutic agents include agents that are effective for the modulation of immune system or associated conditions such as AZT, 3TC, 8-substituted guanosine analogs, 2',3'-dideoxynucleosides, interlcukin II, interferons, such as $\alpha$-interferon, tucaresol, levamisole, isoprinosine and cyclolignans. Certain compounds according to the present invention may be effective for enhancing the biological activity of certain agents according to the present invention by reducing the metabolism or inactivation of other compounds and as such, are co-administered for this intended effect.

Figure 3:
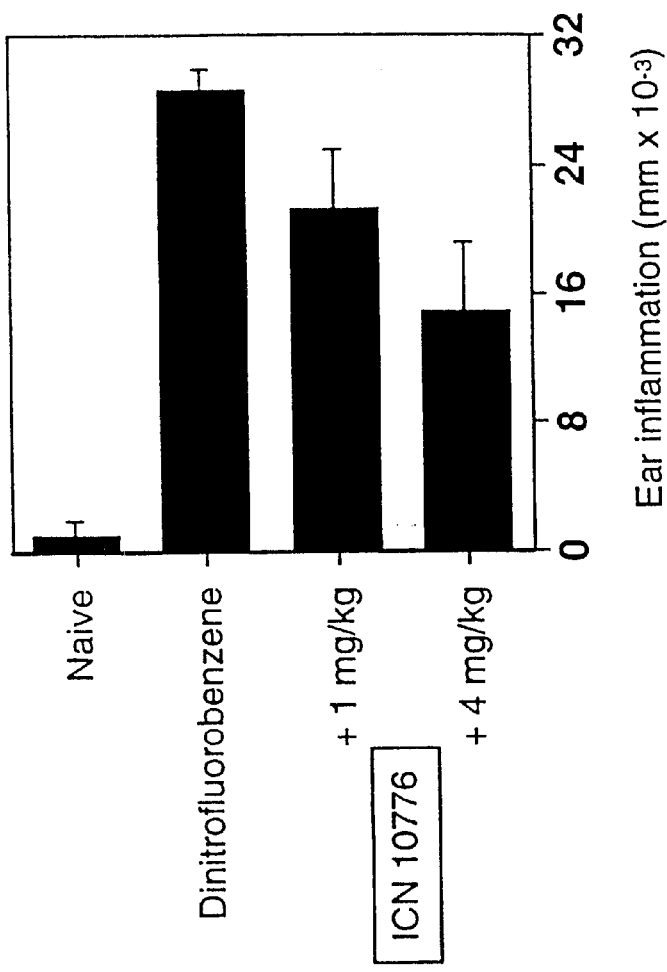
FIG. 3 is a graphical depiction of the effect of some of the compounds according to the present invention on an in vivo response to contact allergen (DNFB) in BALB/C mice.
Figure 4:
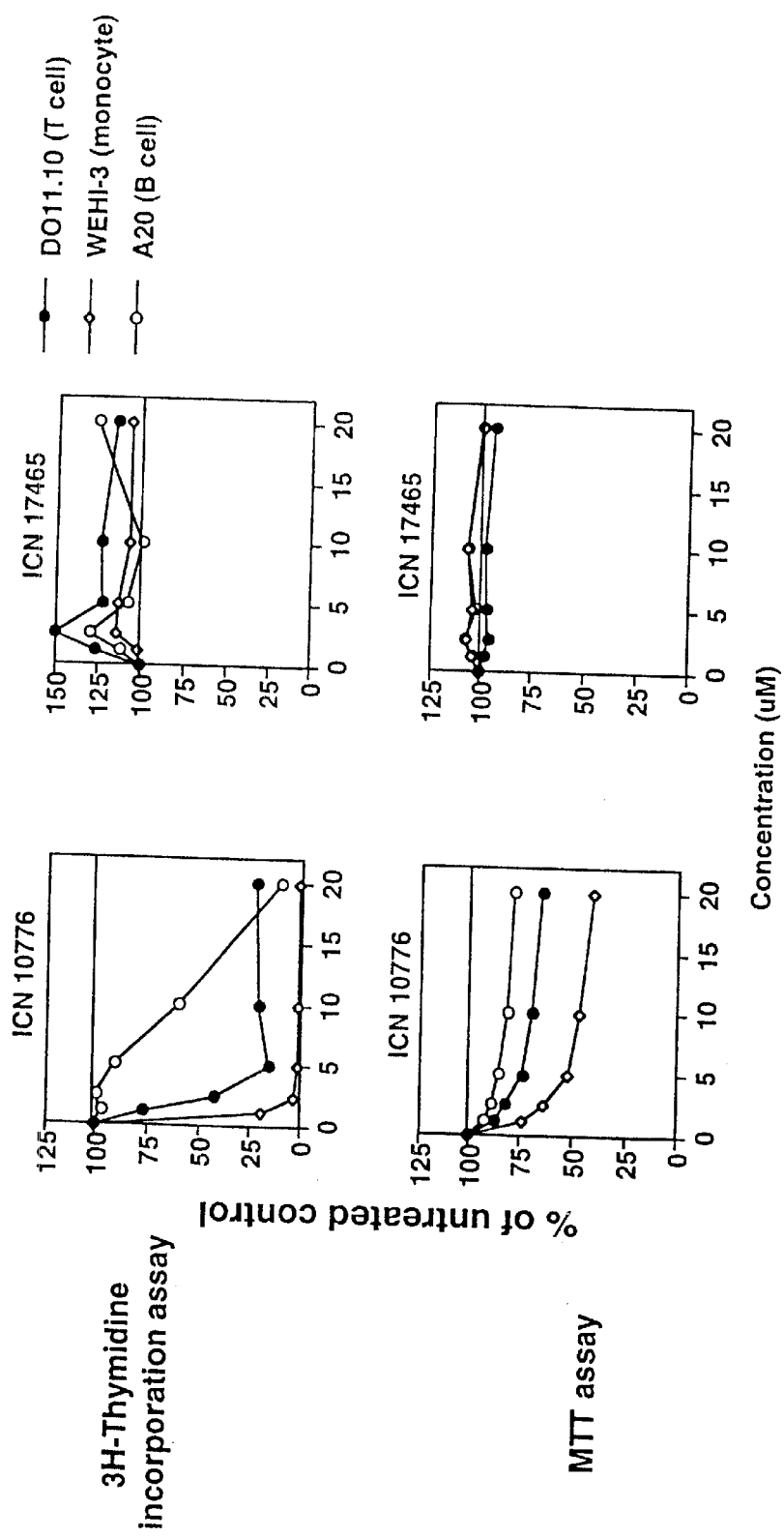
FIG. 4 is a graphical depiction of the effect of some of the compounds according to the present invention on the inhibition of the proliferation of lymphoid cells.

With respect to dosage, one of ordinary skill in the art will recognize that a therapeutically effective amount will vary with the infection or condition to be treated, its severity, the treatment regimen to be employed, the pharmacokinetics of the agent used, as well as the patient (animal or human) treated. (FIG. 2 ) It is contemplated that various alternative dosages are also appropriate, including dosages between 0.5 mg/kg and 0.1 mg/kg and less, but also dosages between 0.5 and 1.0 mg/kg and more. It is further contemplated that while treatment success may be achieved with some viral infections at relatively low plasma concentrations of the compounds of Formula 1 or Formula 2, other viral infections may require relatively high dosages. It is contemplated, however, that an appropriate regimen will be developed by administering a small amount, and then increasing the amount until the side effects become unduly adverse, or the intended effect is achieved. (FIG. 3 )

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

SYNTHESIS 3-cyano-1-(2,3,5-tri-O-acetyl-$\beta$-D-ribofuranosyl)-1, 2,4-tirazole (3)

A round bottom flask containing a mixture of 3-cyano-1, 2,4-triazole (2) (18.82 g, 200 mmol), 1,2,3,5-tetra-O-acetyl- β-D-ribofuranose (1) (63.6 g, 200 mmol) and bis(p-nitrophenyl)phosphate (0.5 g) was placed in a pre-heated oil bath at 160–170° C. The flask was heated under water aspirator pressure (diminished) for 20 min. The acetic acid replaced from the reaction was collected in an ice-cold trap that was placed between the roundbottom flask and the aspirator. After 20 min., the flask was removed from the oil bath and allowed to cool. When the temperature of the flask reached approximately 50–60° C., ethyl acetate (250 ml) was introduced followed by sat.sodium bicarbonate (200 ml) and extracted in ethyl acetate. The organic extract was washed with sodium bicarbonate (2×200 ml), water (200 ml) and brine (200 ml), dried over anhydrous sodium sulfate and evaporated to dryness. The residue was dissolved in a minimum amount of ethyl ether and allowed to cool. Crystallized material was filtered and dried. Yield 56.4 g (80%). MP 96–99° C.; $^1$H NMR (CDCl$_3$): δ 2.11 (s, 3H, COCH$_3$), 2.13 (s, 3H, COCH$_3$), 2.15 (s, 3H, COCH$_3$), 4.22 (dd, 1H), 4.40–4.50 (m, 2H), 5.56 (m, 1H), 5.66 (m, 1H), 6.03 (d, 1H, $J_{1',2'}$=3.3 Hz, H$_1$), 8.40 (s, 1H, C$_5$H). Anal. (C$_{14}$H$_{16}$N$_4$O$_7$) C, H, N.

1-β-D-Ribofuranosyl-1,2,4-tirazole-3-caroxamidine Hydrochloride (4)

3-cyano-1-(2,3,5-tri-O-acetyl-β-D-ribofuranosyl)-1,2,4-tirazole (3) (35.2 g, 100 mmol), NH$_4$Cl (5.35 g, 100 mmol) and anhydrous ammonia (300 ml) was heated in a steel bomb at 85° C. for 18 hr. The steel bomb was cooled to −35° C., opened carefully and the ammonia was evaporated. The residue was crystallized from acetonitrile-ethanol mixture to provide 26.5 g (95%) of 1-β-D-Ribofuranosyl-1,2,4-tirazole-3-caroxamidine Hydrochloride (4). MP 177–179° C. (dec); $^1$H NMR (DMSO-d$_6$); δ 3.50 (m, 1H, C$_5$H), 3.60 (m, 1H, C$_5$H), 3.94 (m, 1H), 4.13 (dd, 1H), 4.35 (m, 1H), 5.00 (bs, 1H), 5.26 (bs, 1H), 5.64 (bs, 1H), 5.81 (d, 1H, $J_{1',2'}$=3.9 Hz, H$_1$), 7.34 (bs, 2H), 8.92 (s, 1H, C$_5$H). Anal. (C$_8$H$_{14}$N$_5$O$_4$Cl) C, H, Cl, N.

Thus, specific embodiments and applications of heterocyclic aromatic compounds have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A method of treatment of a condition selected from the group consisting of an infection, an autoimmume disease, and a cancer in a patient comprising:

administering a compound according to Formula 1 or Formula 2,

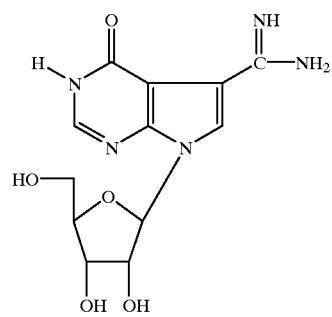

Formula 1

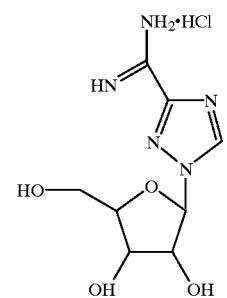

Formula 2 wherein the compound according to Formula 1 has an L-configuration or a D-configuration, and wherein the compound according to Formula 2 has an L-configuration.

2. The method of claim 1 wherein the compound administered is according to Formula 1.

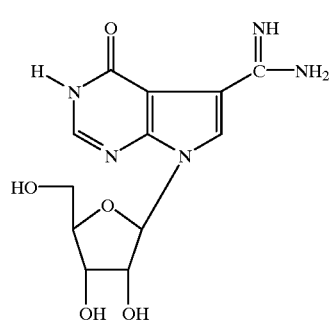

Formula 1

3. The method of claim 1 wherein the compound administered is according to Formula 2.

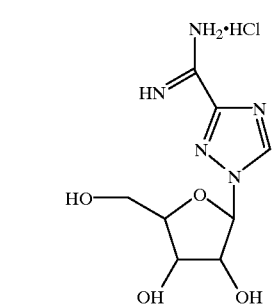

Formula 2

4. The method of claim 1, wherein the condition is an HIV infection.

5. The method of claim 1, wherein the condition is an HCV infection.

6. The method of claim 1, wherein the condition is a Human Papilloma Virus.

7. The method of claim 1, wherein the condition is an HBV infection.

8. The method of claim 1 wherein the condition is giant cell arteritis.

9. The method of claim 1 wherein the step of administering increases a Type 2 response relative to a Type 1 response in the patient.

10. The method of claim 1 wherein the step of administering comprises oral administration.

11. The method of claim 1 wherein the step of administering comprises injection of the L-ribonucleoside.

12. The method of claim 1 wherein the step of administering comprises administering the compound in a dose between 0.1 mg per kg of body weight of the patient and 1.0 mg per kg of body weight of the patient.

* * * * *